United States Patent
Serero et al.

(10) Patent No.: US 7,638,770 B2
(45) Date of Patent: Dec. 29, 2009

(54) METHOD FOR DETECTING A FIRE CONDITION IN A MONITORED REGION

(75) Inventors: Shaul Serero, Rishon-Letsion (IL); David Cohen, Ashkelon (IL); Oded Spector, Tel Aviv (IL); Yechiel Spector, Tel Aviv (IL)

(73) Assignee: Spectronix Ltd., Sderot (IL)

( * ) Notice: Subject to any disclaimer, the term of this patent is extended or adjusted under 35 U.S.C. 154(b) by 0 days.

(21) Appl. No.: 12/053,605

(22) Filed: Mar. 23, 2008

(65) Prior Publication Data

US 2008/0230701 A1    Sep. 25, 2008

Related U.S. Application Data

(60) Provisional application No. 60/896,276, filed on Mar. 22, 2007.

(51) Int. Cl.
G01J 5/02    (2006.01)
(52) U.S. Cl. .............. 250/339.15; 250/339.05
(58) Field of Classification Search .......... 250/338.1, 250/339.01, 339.05, 339.14, 339.15
See application file for complete search history.

(56) References Cited

U.S. PATENT DOCUMENTS

| | | | |
|---|---|---|---|
| 3,653,016 A | 3/1972 | Cormier | |
| 3,665,440 A | 5/1972 | McMenamin | |
| 3,825,754 A | 7/1974 | Cinzori et al. | |
| 3,859,520 A | 1/1975 | Hertzberg et al. | |
| 3,931,521 A | 1/1976 | Cinzori | |
| 4,199,682 A | 4/1980 | Spector et al. | |
| 4,220,857 A | 9/1980 | Bright | |
| 4,296,324 A | 10/1981 | Kern et al. | |
| 4,455,487 A | 6/1984 | Wendt | |
| 4,639,598 A | 1/1987 | Kern et al. | |
| 4,679,156 A | 7/1987 | Kern et al. | |
| 4,691,196 A | 9/1987 | Kern et al. | |
| 4,765,413 A | 8/1988 | Spector et al. | |
| 4,769,775 A | 9/1988 | Kern et al. | |
| 4,983,853 A | 1/1991 | Davall et al. | |
| 5,311,167 A | 5/1994 | Plimpton et al. | |
| 5,373,159 A * | 12/1994 | Goldenberg et al. | ... 250/339.15 |
| 5,612,676 A | 3/1997 | Plimpton et al. | |
| 6,518,574 B1 * | 2/2003 | Castleman | ............. 250/339.15 |
| 6,756,593 B2 * | 6/2004 | Nakauchi et al. | ........ 250/339.15 |
| 6,914,246 B2 * | 7/2005 | Servaites et al. | ........ 250/339.15 |
| RE39,081 E * | 5/2006 | Thomas | ...................... 340/578 |

(Continued)

*Primary Examiner*—David P Porta
*Assistant Examiner*—David S Baker
(74) *Attorney, Agent, or Firm*—Mark M. Friedman

(57) ABSTRACT

A method of detecting a fire condition in a monitored region including the operations of: concurrently monitoring the region using: a plurality of fire combustion product emission band sensors, each band sensor sensitive to radiation within a respective waveband which includes at least part of a respective fire combustion product emission band of a plurality of fire combustion products, the plurality of fire combustion products equal to n; a first reference band sensor sensitive to radiation within a first reference waveband which includes at least some wavelengths shorter than the n fire combustion product emission bands; and a second reference band sensor sensitive to radiation within a second reference waveband which includes at least some wavelengths longer than the n fire combustion product emission bands; and using the band sensors to obtain n+2 measurement values of radiation intensity emitted from the monitored region in determining the presence or absence of the fire condition.

14 Claims, 2 Drawing Sheets

U.S. PATENT DOCUMENTS

| | | |
|---|---|---|
| 7,112,796 B2 * | 9/2006 | Brown et al. ........... 250/339.15 |
| 7,202,794 B2 | 4/2007 | Huseynov et al. |
| 7,335,885 B2 * | 2/2008 | Wong .................... 250/339.15 |
| 2006/0017578 A1 * | 1/2006 | Shubinsky et al. .......... 340/578 |

* cited by examiner

METHOD FOR DETECTING A FIRE CONDITION IN A MONITORED REGION

This application claims priority from U.S. Provisional Application No. 60/896,276, filed 22 Mar. 2007, whose disclosure is incorporated herein by reference.

FIELD AND BACKGROUND OF THE INVENTION

The present invention relates to a method for detecting a fire condition in a monitored region, and in particular, it concerns a method for detecting organic and inorganic fuel fires at relatively long ranges and/or for detecting relatively small organic and inorganic fires.

Existing optical flame detectors are limited in their detection range and in their spectral response to either organic fuel flames (such as flames having a $CO_2$ spectral peak) or inorganic fuel flames (such as flames having a $H_2O$ spectral peak). One problem in detecting fire conditions, particularly at long detection ranges or for small fires, is a high false alarm rate. The detection range can be increased by increasing system sensitivity, e.g. by appropriately setting an amplification level and/or a threshold level. However, an increase in sensitivity also tends to increase the false alarm rate, which is caused by spurious radiation sources such as: sunlight; artificial light; welding; electrical heaters; ovens; etc., or by other sources of radiation "noise". Such spurious radiation sources might not be intense enough to activate short-range detectors, but they may be sufficient to activate a detector whose sensitivity has been increased for an increased detection range.

A false alarm can result in a costly discharge of a fire extinguisher. Furthermore, if the fire extinguisher is of the type requiring replacement before it can be reused, the false alarm can serve to effectively disable the fire extinguisher system until the extinguisher system has been replaced.

A number of attempts have been made to increase the range of a fire detector system without substantially increasing the false alarm rate. Some systems utilize two sensors in different spectral ranges, as described in U.S. Pat. Nos.: 3,653,016, 3,665,440, 3,825,754, 3,931,521, 4,639,598 and 4,983,853, whose disclosure is incorporated herein by reference Other systems utilize an AC coupling and a level ratio test, as described in U.S. Pat. No. 4,455,487, whose disclosure is incorporated herein by reference. In another system, the detector examines the frequency characteristics of monitored signals produced by a sensor to distinguish between fire-emitted radiation and spurious radiation.

European patent EP0926647B1 and U.S. Pat. No. 5,373,159, whose disclosure is incorporated herein by reference, describe a triple-IR method for detecting fire condition using three sensors, each sensitive to a different wavelength bands. The first band is sensitive to wavelengths, which include the $CO_2$ emission band, and the second and third bands are sensitive to wavelengths shorter and longer than the $CO_2$ band. This method is reliable in distinguishing between the radiation emitted by flames having hot $CO_2$ content (e.g. hydrocarbon fires) and other environmental and spurious radiation sources. The method allows increased sensitivity and speed of detection while keeping the probability of false alarms low. However, the method only allows detection of flames from organic materials (hydrocarbons) which emit $CO_2$ in the combustion process.

Flames from fuels such as Hydrogen, Hydrazine, Hydroxyl fuels and Ammonia do not emit any $CO_2$ in the combustion process, but they do emit large amounts of hot water vapors. Flames from these sources can be detected using a similar triple-IR method, where the first sensor is sensitive to wavelengths in one of the water IR emission bands (for example at wavelengths around 2.7 microns). The second and third sensors are sensitive to wavelengths shorter and longer than the water emission band. Such a method can enable detection of water vapor emitting flames with great sensitivity and with a low probability of false alarm. However, this method does not allow detection of flames that do not produce enough water vapor to emit a significant spectral peak in the water emission band.

The two methods described above, namely for detection of $CO_2$-emitting flames and water vapor-emitting flames, do not distinguish efficiently between flames that should be detected and other sources of hot $CO_2$ and/or water vapor, such as steam pipes, industrial burners, and ovens. The characteristic which differentiates between flames and such hot gas sources is the hot gas (i.e. fire combustion product) temperature. The temperature of the gas in the combustion process inside the flame is typically much higher than that of a gas emitted from spurious sources such as steam pipes and ovens. The temperature difference between these different sources has implications on source emission spectral characteristics. For higher temperatures, the gas emits radiation with an intensity more concentrated in shorter wavelengths. For lower temperatures, the radiation intensity is more concentrated in longer wavelengths. Unfortunately, the monitored wavelength bands of the three sensors in the methods described hereinabove are not spread far enough across the spectrum to effectively discriminate between flames and spurious hot sources. If these bands are moved further apart from each other, it would be possible to differentiate between flame temperatures and hot vapor/$CO_2$ temperatures; but the reliability of detection of the $CO_2$ or water vapor spectral peaks would be severely compromised.

Some methods exist (e.g. U.S. Pat. Nos. 5,612,676 and 5,311,167, whose disclosure is incorporated herein by reference) for detection of both hydrocarbon flames (such as $CO_2$ emitting flames) and some non-hydrocarbon flames (e.g. Hydrogen or Ammonia). However, these methods are either less sensitive to the detection of a fire or more prone to false alarms than the triple-IR methods noted hereinabove. The tendency to be less sensitive and/or more prone to false alarms is due to the fact that in these methods not enough data is gathered from the sensors to confidently distinguish between flames (having intensity peak at the $CO_2$ or water vapor emission wavebands) and other sources that do not have these spectral peaks.

There is therefore a need for systems and/or method with:
high sensitivity (ability to sense at longer detection ranges and/or more discriminately);
high selectivity between organic and inorganic fires; and
low false alarm/false detections.

SUMMARY OF THE INVENTION

The present invention is a method for detecting a fire condition in a monitored region, and in particular, it concerns a method for detecting organic and inorganic fuel fires at relatively long ranges and/or for detecting relatively small organic and inorganic fires.

According to the teachings of the present invention there is provided, a method of detecting a fire condition in a monitored region including the operations of: concurrently monitoring the region using: a plurality of fire combustion product emission band sensors, each band sensor sensitive to radiation within a respective waveband which includes at least part of a respective fire combustion product emission band of a plurality of fire combustion products, the plurality of fire combustion products equal to n; a first reference band sensor sensitive to radiation within a first reference waveband which includes at least some wavelengths shorter than the n fire combustion product emission bands; and a second reference band sensor sensitive to radiation within a second reference waveband which includes at least some wavelengths longer than the n fire combustion product emission bands; and using the band sensors to obtain n+2 measurement values of radiation intensity emitted from the monitored region in determining the presence or absence of the fire condition. Preferably, concurrently monitoring the region is performed using a single detector having the plurality of fire combustion product emission band sensors. Most preferably, the n+2 measurement values include: n measurement values obtained from the emission band sensors; one measurement value obtained from the first reference band sensor; and one measurement value obtained from the second reference band sensor and from which detection parameters are calculated, which are evaluated against at least one threshold in determining the presence or absence of the fire condition.

Typically, the detection parameters include two respective reference ratios calculated for each of the n measurement values: a first reference ratio between respective n measurement values and the measurement value from the first reference band sensor; and a second reference ratio between respective n measurement values and the measurement value from the second reference band sensor. Most typically, the detection parameters further include ratios calculated for each of the n measurement values, between a respective measurement value and other measurement values. Preferably, the detection parameters further include a first-to-second reference ratio calculated between respective measurement values from the first and second reference band sensors. Most preferably, the detection parameters include two respective correlation values calculated for each of the n measurement values, a first reference correlation between respective n measurement values and the measurement value from the first reference band sensor, and a second reference correlation between respective n measurement values and the measurement value from the second reference band sensor. Typically, individual fire combustion products are identified. Most typically, the at least one threshold includes a threshold value associated with respective measurement values and with respective correlation values.

Preferably, the at least one threshold value is determined by at least one chosen from a list including: empirical means and non-empirical means. Most preferably, n=2 and the plurality of fire combustion products is chosen from a list including: $CO_2$ and $H_2O$, and $CO_2$ and OH, and $SO_2$ and $H_2O$, and $SO_2$ and OH, and $NO_2$ and $H_2O$, and $NO_2$ and OH. Typically, n=3 and the plurality of fire combustion products is: $CO_2$ and $H_2O$ and $SO_2$, or $NO_2$ and $H_2O$ and $SO_2$. Most typically, respective band sensors are sensitive to infrared radiation and or to ultraviolet radiation.

Preferably, n=2 and: the plurality of fire combustion product emission band sensors includes a first band sensor [$IR_1$], having a sensitivity to a waveband which includes part of the 4.2 to 4.7 μm $CO_2$ emission band, and a second band sensor [$IR_2$], having a sensitivity to a waveband which includes at least part of the 2.4 to 3.1 μm $H_2O$ emission band; the first reference sensor [$IR_3$], having a sensitivity to waveband, which includes at least some wavelengths shorter than the wavebands of sensors [$IR_1$] and [$IR_2$]; and the second reference sensor [$IR_4$], having a sensitivity to waveband, which includes at least some wavelengths longer than the wavebands of sensors [IR1] and [IR2]. Most preferably, individual fire combustion products are identified.

According to the teachings of the present invention there is further provided, a method of detecting a fire condition in a monitored region including the operations of: concurrently monitoring the region using: a plurality of fire combustion product emission band sensors, each band sensor sensitive to radiation within a respective waveband which includes at least part of a respective fire combustion product emission band of a plurality of fire combustion products, the plurality of fire combustion products equal to n; a first reference band sensor sensitive to radiation within a first reference waveband which includes only wavelengths shorter than the n fire combustion product emission bands; and a second reference band sensor sensitive to radiation within a second reference waveband which includes only wavelengths longer than the n fire combustion product emission bands; and using the band sensors to obtain n+2 measurement values of radiation intensity emitted from the monitored region in determining the presence or absence of the fire condition. Preferably, concurrently monitoring the region is performed using a single detector having the plurality of fire combustion product emission band sensors. Most preferably, the n+2 measurement values include: n measurement values obtained from the emission band sensors; one measurement value obtained from the first reference band sensor; and one measurement value obtained from the second reference band sensor and from which detection parameters are calculated, which are evaluated against at least one threshold in determining the presence or absence of the fire condition.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
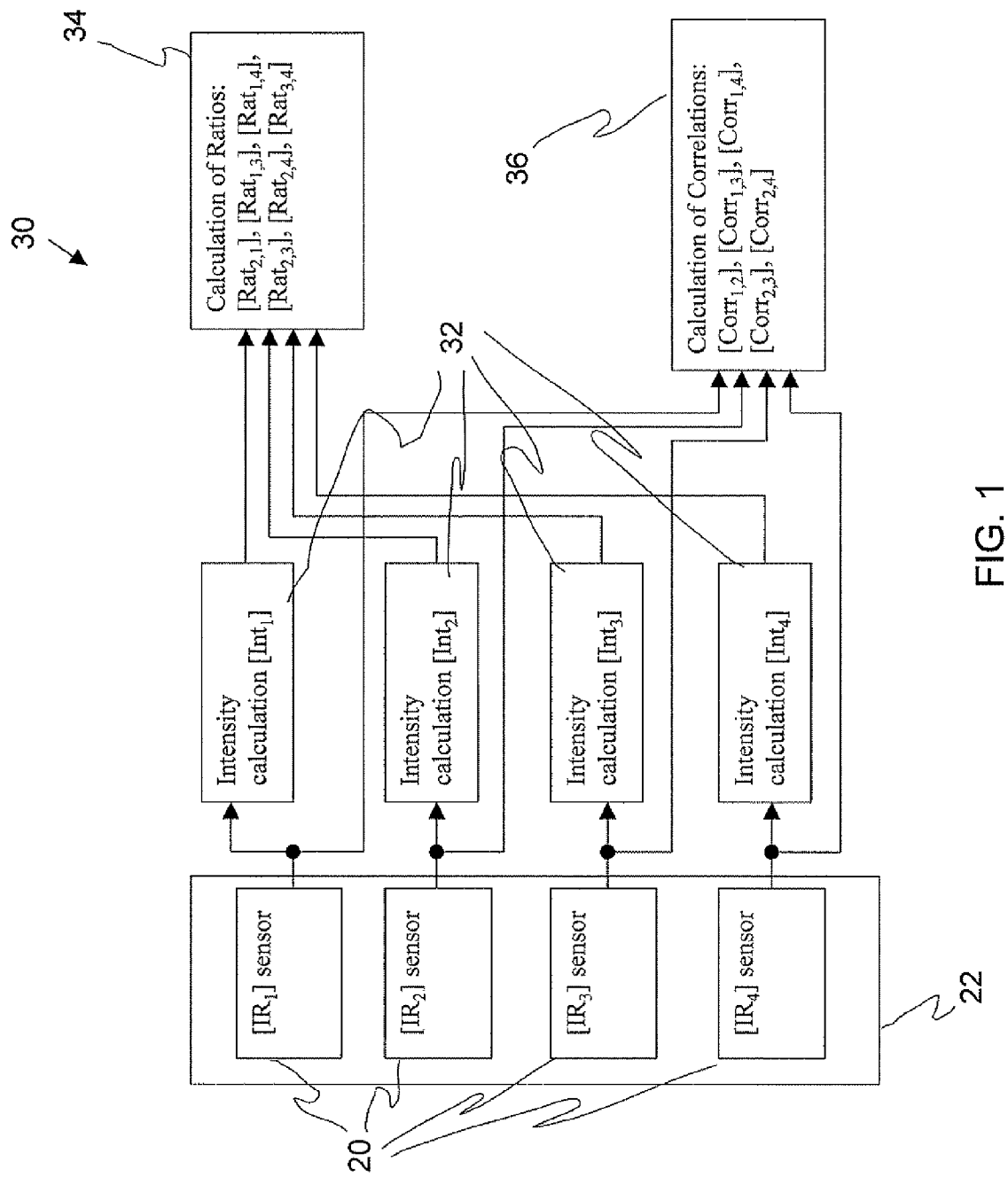
FIG. 1 is a block diagram illustrating output from sensors and calculation of detection parameters, in accordance with an embodiment of the current invention.

The present invention is a method for detecting a fire condition in a monitored region, and in particular, it concerns a method for detecting organic and inorganic fuel fires at relatively long ranges and/or for detecting relatively small organic and inorganic fires.

The principles and operation of a method for detecting a fire condition in a monitored region according to the present invention may be better understood with reference to the drawings and the accompanying description.

One of the embodiments of the present invention allows highly sensitive and reliable detection of both hydrocarbon flames and non-hydrocarbon flames that emit large amounts of water vapor in their combustion process, with extremely low probability of false alarms, even from other sources of hot $CO_2$ or water vapor, and at a relatively low cost.

The low cost afforded by an embodiment of the present invention is obtained by being able to use a single detector unit with four sensors for detection of fires of types and from distances that would alternatively require the use of at least two detectors, and a larger total number of sensors.

As is noted further hereinbelow, the use of additional sensors, preferably with the use of a single detector, allows scaling of configurations of embodiments of the present invention to allow economical and reliable detection of more complicated fire types and/or of additional gases from fire combustion products.

In the specification and the claims hereinbelow, the following terms are defined.

"Fire combustion product" is used to mean a product, usually of a gaseous form, originating from a fire which may be detected by embodiments of the present invention. As such, the term "gas" is used interchangeably hereinbelow in reference to a fire combustion product.

"Intensity value" is intended to mean a value that is calculated from output of a sensor sensing radiation intensity. An intensity value may be derived from a single instantaneous measurement or it may be a series of measurements over a time interval. The calculated value may be the result of any one or a combination of: electronic filtering and amplification, digital filtering, and one or more mathematical operations and/or transformations.

An alternative expression for "intensity value" used herein is "measurement value".

"Sensor configuration" is used to include additional components frequently closely associated with sensors, as known in the art, such as but not limited to filters and/or other electro optic components. As such, "sensor configuration" and "sensor" are intended to have the same meaning.

"Detection parameters" is intended to mean parameters expressed as ratios between respective intensity values and/or parameters expressed as correlations between respective intensity values.

"Ratio or ratio value" is intended to mean a value reflecting a measure of the relation between two measurement values. A ratio may be expressed simply as a division of one measurement value by another or by any other function or transformation between the two measurement values.

"Correlation or correlation value" is intended to mean a value that relates to the similarity of the temporal behavior of two measurement values being compared. A correlation may be expressed as any known statistical function or other function or transformation between the two measurement values.

"Threshold" is intended to mean a value that is determined by empirical or by non-empirical means by which one or more detection parameters are evaluated, so as to determine a fire condition or not.

"Waveband" is used interchangeably with "wavelength band", both expressions intended to mean a characteristic range of wavelengths.

"Emission band" of a particular fire combustion product is intended to mean a waveband comprising only those wavelengths which a particular fire combustion product emits and which are incident on a fire detector with significant intensity. In this sense, significant intensity, and therefore wavelengths included in the emission band itself may vary according to the considered application, such as but not limited to: fire type, fire distance from the detector, expected atmospheric conditions, and expected background radiation.

"Includes", when used in reference to a waveband, is intended to mean the inclusion of a waveband in its entirety or partially, and the inclusion of the waveband with or without the inclusion of additional wavebands. For example, "A waveband, which includes the $CO_2$ emission band" is intended to mean any waveband, which includes the entire $CO_2$ emission band, or which includes only parts of the $CO_2$ emission band. In this exemplary case, when the term "includes" is used, the waveband may include other wavelengths outside the $CO_2$ emission band as long as the waveband also includes at least a part of the $CO_2$ emission band.

Finally, in this exemplary case, using the term "includes", the waveband may not solely include wavelengths outside the $CO_2$ emission band.

Reference is presently made to FIG. 1, which is a block diagram illustrating output from sensor configurations 20 and calculation of detection parameters 30, in accordance with an embodiment of the current invention. The sensors and wavelengths noted immediately hereinbelow refer to an embodiment of the present invention taking advantage of infrared (IR) radiation, although other radiation having other wavelengths, such as but not limited to ultraviolet radiation may be employed. In an embodiment of the current invention, sensor configurations 20 are part of a single detector 22, thereby reducing the sensor configuration cost.

The four sensor configurations, indicated as $[IR_1]$, $[IR_2]$, $[IR_3]$, and $[IR_4]$ have the following functions.

$[IR_1]$—The sensor configuration, which may include a filter (not shown), that is sensitive to radiation variations within a wavelength band that includes at least part of one of the $CO_2$ emission bands.

$[IR_2]$—The sensor configuration, which may include a filter (not shown), that is sensitive to radiation variations within a wavelength band that includes at least part of one of the water vapor emission bands.

$[IR_3]$—The sensor configuration, which may include a filter (not shown), that is sensitive to radiation variations within a wavelength band, which includes wavelengths shorter than both those of the $CO_2$ emission bands and the water vapor emission bands. The selected wavelength band may include wavelengths within the $CO_2$ wavebands; however the portion of measured intensity, corresponding to the $CO_2$ bands, compared to the total measured intensity, must be lower than the portion of the measured intensity corresponding to the $CO_2$ wavebands, of the $[IR_1]$ waveband. Similarly, the selected wavelength band may include wavelengths within the water vapor wavebands; however the portion of measured intensity, corresponding to the water vapor wavebands, compared to the total measured intensity, must be lower than the portion of the measured intensity, corresponding to the water wavebands, of the $[IR_2]$ waveband.

Alternatively, the selected wavelength band may include only wavelengths shorter than both those of the $CO_2$ emission bands and the water vapor emission bands.

$[IR_4]$—The sensor configuration, which may include a filter (not shown), that is sensitive to radiation variations within a wavelength band, which includes wavelengths, longer than both the $CO_2$ and water vapor emission bands. The selected wavelength band may include wavelengths within the $CO_2$ wavebands; however the portion of measured intensity, corresponding to the $CO_2$ bands, compared to the total measured intensity, must be lower than the portion of the measured intensity corresponding to the $CO_2$ bands, of the $[IR_1]$ waveband. Similarly, the selected wavelength band may include wavelengths within the water vapor wavebands; however the portion of measured intensity, corresponding to the water vapor wavebands, compared to the total measured intensity, must be lower than the portion of the measured intensity, corresponding to the water wavebands, of the $[IR_2]$ waveband.

Alternatively, the selected wavelength band may include only wavelengths longer than both those of the $CO_2$ emission bands and the water vapor emission bands.

Output from respective sensor configurations $[IR_1]$, $[IR_2]$, $[IR_3]$ and $[IR_4]$ is then passed to respective intensity calculation modules 32, to form respective measurement values of the emitted radiation. Output from respective sensor configurations is typically filtered and amplified and then transformed into digital format and further filtered by software when transferred to the intensity calculation modules. For each of the transformed outputs a respective measurement value ($[Int_1]$, $[Int_2]$, $[Int_3]$ and $[Int_4]$) is calculated. The calculation may be performed in several ways, for example: using the absolute value of the output, or using the square of the output value. The measurement value may be calculated according to an instantaneous value of the output, or the measurement value may be calculated by integrating the output over a certain period, with or without weighting. Other calculation methods such as the use of the Fourier transform (FT) or wavelet calculations may also be employed to obtain several measurement values for each sensor configuration, thereby providing an analysis of the intensity in several bands of frequencies, or of other similar merits. Another example of an intensity calculation module calculation is the use of an autocorrelation function between the output and itself.

Using the measurement values ($[Int_1]$, $[Int_2]$, $[Int_3]$ and $[Int_4]$), ratio values and correlation values are calculated in ratio calculation modules 34 and correlation calculation modules 36, respectively. These values are measures of the relation between pairs of sensors' signals. Ratios can be calculated as a simple division between measurement values. For example, $[Rat_{ij}]$ is an expression of the ratio between measurement value i and measurement value j. $[Rat_{ij}]$ may be calculated as $[Rat_{ij}]=[Int_i]/[Int_j]$. Other functions, besides a simple division, can also be used to calculate $[Rat_{ij}]$, so that it expresses a measure of measurement value i compared to the measurement value j. Examples of other such functions, for illustration purposes only, are:

$$[Rat_{ij}]=([Int_i]-[Int_j])/[Int_j]; [Rat_{ij}]=[Int_i]/([Int_i]+[Int_j]); [Rat_{ij}]=\log([Int_i]/[Int_j]): \text{ and } [Rat_{ij}]=[Int_i]^2/([Int_i]^2+[Int_j]^2).$$

In an embodiment of the current invention, a ratio is calculated for each pair of measurement values, corresponding to each pair of sensor configurations. $[Rat_{ij}]$ is therefore expressed as: $[Rat_{2,1}]$, $[Rat_{1,3}]$, $[Rat_{1,4}]$, $[Rat_{2,3}]$, $[Rat_{2,4}]$ and $[Rat_{3,4}]$.

Correlation values $[Corr_{ij}]$ are calculated in correlation calculation modules 36, between pairs of respective measurement values, such as between measurement value i and measurement value j. $[Corr_{ij}]$ can be calculated in any way that results in a value that relates to the similarity of the temporal behavior of the two signals. For example, the value of a mathematical correlation function between the two signals as functions of time can be obtained. $[Corr_{ij}]$ can then be defined and calculated as the value of the correlation function at 0, or as a weighted average of the correlation function over a range of values.

Another example of a calculation for the correlation value $[Corr_{ij}]$ is by evaluating a certain time period and changing the sign (i.e. "+" or "−") of the measurement value i according to measurement value j. In other words, when measurement value j has a negative value, the sign of measurement value i is reversed, and when measurement value j has a positive value, the sign of measurement value i is retained. The measurement value with the reversed sign (i) is then integrated over the time period to obtain a value for the correlation.

The correlation value can be calculated symmetrically, i.e. so that in every case $[Corr_{ij}]=[Corr_{j,i}]$, or it may be calculated non-symmetrically. The correlation can also be calculated in a normalized fashion, i.e. so that the value is assured to be in a certain range, for example 0 to 1. It can also be calculated without normalization.

In one embodiment of the current invention, correlation values are calculated as: $[Corr_{1,2}]$, $[Corr_{1,3}]$, $[Corr_{1,4}]$, $[Corr_{2,3}]$ and $[Corr_{2,4}]$. According to one embodiment of the current invention $CO_2$ emission bands and $H_2O$ emission bands are sensed and respective measurement values are analyzed. Using these two exemplary gases, appropriate emission bands for sensor configurations $[IR_1]$, $[IR_2]$, $[IR_3]$ and $[IR_4]$ could be 4.3 to 4.6 μm, 2.5 to 2.9 μm, 2.0 to 2.6 μm, and 4.5 to 5.0 μm, respectively. Different wavelength emission bands can also be used, as long as the $[IR_1]$ waveband includes at least part of the 4.2 to 4.7 μm $CO_2$ band, the $[IR_2]$ waveband includes at least part of the 2.4 to 3.1 μm water vapor band, the $[IR_3]$ waveband includes at least some wavelengths lower than wavebands of both $[IR_1]$ and $[IR_2]$, and the $[IR_4]$ waveband includes at least some wavelengths higher than wavebands of both $[IR_1]$ and $[IR_2]$. The wavelength bands of $[IR_3]$ and $[IR_4]$ may include wavelengths within the 4.2 to 4.7 μm $CO_2$ band, as long as the portion of measured intensity, which results from 4.2 to 4.7 μm band, compared to the total measured intensity, is lower than the similar portion of the waveband of $[IR_1]$. Similarly, the wavelength bands of $[IR_3]$ and $[IR_4]$ may include wavelengths within the 2.4 to 3.1 μm water vapor band, as long as the portion of measured intensity, which results from the 2.4 to 3.1 μm band, compared to the total measured intensity, is lower than the similar portion of the waveband of $[IR_2]$.

Alternatively or optionally, as described previously hereinabove, the $[IR_3]$ waveband includes only wavelengths lower than wavebands of both $[IR_1]$ and $[IR_2]$, and the $[IR_3]$ waveband includes only wavelengths shorter than wavebands of both $[IR_1]$ and $[IR_2]$.

Other fire combustion products or other combinations of fire combustion products, such as but not limited to: $CO_2$ and $H_2O$, $CO_2$ and $SO_2$, $NO_2$ and $CO_2$, $SO_2$ and $H_2O$, $NO_2$ and $H_2O$, $NO_2$ and $SO_2$, and $OH$ and $CO_2$ can be used in other embodiments of the present invention, with appropriate emission bands for sensor configurations $[IR_1]$, $[IR_2]$, $[IR_3]$ and $[IR_4]$, mutatis mutandis.

Figure 2:
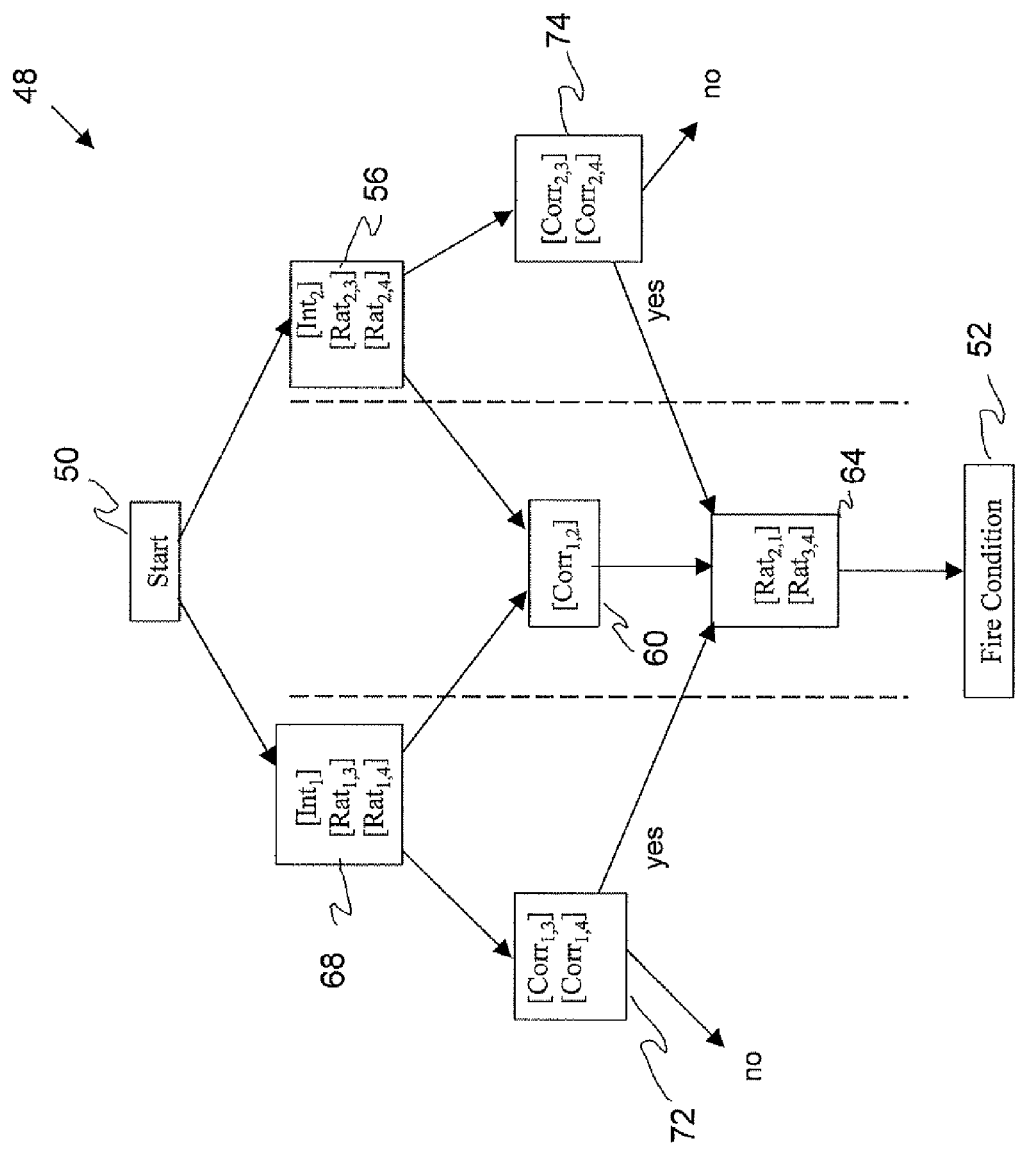
FIG. 2 is a flow chart indicating steps to determine a fire condition, using the detection parameters shown in FIG. 1 and in accordance with an embodiment of the current invention.

Reference is now made to, FIG. 2, which is a flow chart indicating steps to determine a fire condition, using the detection parameters shown in FIG. 1 and in accordance with an embodiment of the current invention. After the measurement values and detection parameters are obtained as described hereinabove, they are used to determine whether there is a fire condition or not —otherwise referred to in the specification claims which follow as "to detect a fire" or "to detect a fire condition". The determination or decision as to whether there is a fire condition or not is based on a comparison of some or all of the detection parameters according to a predetermined threshold value (not shown in the current figure). The threshold value is typically determined in an empirical process for a given detection parameter, as described further hereinbelow. Alternatively or optionally, the threshold value may be determined in a non-empirical manner.

In embodiments of the current invention, not all detection parameters need to be evaluated against respective threshold values or not all detection parameters need to pass respective threshold values for a determination to be made that there is a fire condition. There can be several scenarios or heuristic paths which can lead to the decision that there is a fire condition. One such heuristic path 48 is shown in FIG. 2. In the exemplary heuristic path shown, a fire condition is declared if there is at least one path from the Start 50 to Fire Condition 52, in which all the variables/evaluations, passed on the way, fulfill their respective thresholds. Heuristic path 48 is typically performed repetitively and/or iteratively as frequently as many times per second, with step 56 $[Int_2]$, $[Rat_{2,3}]$, $[Rat_{2,}$ 4] and step 68 [$Int_1$], [$Rat_{1,3}$], [$Rat_{1,4}$] and subsequent steps being calculated each time to make a determination of (or "to declare") a fire condition.

For example, if step 56, [$Int_2$], [$Rat_{2,3}$], [$Rat_{2,4}$], step 60 [$Corr_{1,2}$], and step 64, [$Rat_{2,1}$] [$Rat_{3,4}$], all fulfill their threshold conditions (meaning respective steps yields a "yes" condition), fire condition 52 is declared regardless of the results ("yes" or "no") of other steps, namely steps 74, 68 and 72. Alternatively, fire condition 52 is declared, if step 68, [$Int_1$], [$Rat_{1,3}$], [$Rat_{1,4}$], a step 72 [$Corr_{1,3}$], [$Corr_{1,4}$] and step 64, [$Rat_{2,1}$] [$Rat_{3,4}$], all fulfill their threshold conditions (meaning respective steps yields a "yes" condition), regardless of the results ("yes" or "no") of the other steps, namely 56, 60 and 74). Other possibilities to determine a fire condition exist, such as via a "yes" result of step 74 [$Corr_{2,3}$], [$Corr_{2,4}$] to declare fire condition 52, as indicated in the figure.

The arrows emanating from step 56 and 68 indicate that the respective following steps, i.e. 74, 60, and 72 are evaluated without regard to the results of steps 56 and 68.

The two vertical dotted lines shown in FIG. 2 identify three regions in the figure. Using the previous examples of fires with $CO_2$ and with hot water vapor, the leftmost region represents conditions relating to the detection of fires that emit large amounts of hot $CO_2$ (for example, hydrocarbon fires). The rightmost region represents conditions relating to the detection of fires that emit large amounts of hot water vapor (for example hydrogen fires). The central region includes conditions common to fire types exhibiting both $CO_2$ and hot water vapor.

As shown in FIG. 2, a fire condition cannot be declared if the thresholds for step 64 are not fulfilled. In step 64, thresholds are evaluated to compare the measured radiation at shorter wavelengths to the measured radiation at longer wavelengths. If the source of radiation is a gas from a flame, then the high temperatures of the flame gas yield emissions having higher intensity in lower wavelengths, and therefore [$Rat_{2,1}$] and [$Rat_{3,4}$] have relatively high values. If the source of radiation is $CO_2$ gas or water vapor at temperatures significantly lower than those typically found in flames, the emitted radiation is mainly in longer wavelengths, and therefore [$Rat_{2,1}$] and [$Rat_{3,4}$] have relatively low values.

By testing obtained values of [$Rat_{2,1}$] and [$Rat_{3,4}$] for different types of real flames, sensed from different sensing distances, and comparing the values to those obtained for other (non-flame) $CO_2$ and water vapor sources, respective thresholds are determined to reliably distinguish between a flame and a lower temperature $CO_2$ or water vapor source. In this manner, reliability of the fire detection is significantly increased.

Embodiments of the present invention can indicate the type of fire detected. For example, if the fire condition is determined through the leftmost region in FIG. 2, then a $CO_2$-emitting fire is indicated. Similarly, if the fire condition is determined through the rightmost region in FIG. 2, then a water vapor ($H_2O$)-emitting fire is indicated.

Embodiments of the current invention can be similarly used to determine a fire condition for more than two fire combustion products, where each combustion product has a corresponding sensor (having respective sensing wavebands); a measure of intensity is formed for each combustion product; and the appropriate ratios and correlations between each of the combustion product sensor's signals and both reference bands are formed.

Similarly, embodiments of the present invention can indicate the type of fire detected when there are more than two fire combustion products. If the fire condition is determined through a detection heuristic path testing the measure of intensity of a respective fire combustion product, then the respective fire combustion product-emitting fire is indicated.

Determination of Threshold Values For Various Combustion Products

As noted hereinabove, detection thresholds (for intensities, ratios, and correlations) may be determined by empirical experimental means. In these experiments, sensors with the specifically designed wavelength bands monitor different fire and non-fire radiation sources. Some examples of experiments and a discussion of various combustion products follow.

It is important to repeat an experiment several times for each source with different conditions. Such conditions that could influence the results significantly are: the distance to the source; the source's size; and ambient conditions (humidity, temperature, aerosols, etc.). Obviously, measured intensities are greatly affected by the source size and the distance. Additionally, the ratios are significantly influenced by the distance to the source and ambient conditions, as these variables influence radiation attenuation by the atmosphere.

In one example, an experiment was performed in which thresholds for $Rat_{1,2}$ and $Rat_{3,4}$ were determined for the wavebands for [$IR_1$], [$IR_2$], [$IR_3$] and [$IR_4$] as noted hereinabove, namely 4.3 to 4.6 μm, 2.5 to 2.9 μm, 2.0 to 2.6 μm, and 4.5 to 5.0 μm, respectively (wavebands typical of an embodiment for detecting Hydrogen, and Hydrocarbon flames). Table 1 lists different sources that were tested, and the range of values (unit-less) measured for $Rat_{1,2}$ and $Rat_{3,4}$ for the sources:

TABLE 1

| Source | $Rat_{1,2}$ | $Rat_{3,4}$ |
| --- | --- | --- |
| Gasoline - 0.3 × 0.3 m² pan fire | 0.15-0.4 | 4-7 |
| Ethyl Alcohol - 0.3 × 0.3 m² pan fire | 0.5-4 | 0.4-1.3 |
| Hydrogen - 0.2 m wide, 0.5 m high flame | 0.003-0.001 | 1.8-2.5 |
| Gasoline engine exhaust emission | 4-30 | 0.01-0.05 |
| Warm water steam | 3-7 | 0.001-0.004 |

Table 1 shows that for $Rat_{3,4}$ there is a clear distinction between fire and non-fire sources. For the fire sources, $Rat_{3,4}$ was larger than 0.4 in all cases, while for non-fire sources it was smaller than 0.05 in all cases. Therefore, the threshold used for $Rat_{3,4}$ can be any value between 0.05 and 0.4. In one embodiment of the present invention, $Rat_{3,4}$ is chosen as 0.1, meaning that any case where $Rat_{3,4}$ is lower than 0.1 would not be considered a fire (an alarm would not be issued for such a case).

For $Rat_{1,2}$ the distinction is not that strong. For fire sources the data shows it was less than 4 in all cases, and for non-fire sources it was larger than 3 in all cases. However, in most cases, non-fire sources yielded $Rat_{1,2}$ values of 5 and higher. Therefore, the an embodiment of the present invention has 5 as the higher threshold, meaning that any case where $Rat_{1,2}$ is higher than 5 would not be considered a fire (an alarm would not be issued for such cases). This corresponds to defining a threshold for $Rat_{2,1}$ (where $Rat_{2,1}=1/Rat_{1,2}$), in which a value lower than 0.2 would not be considered a fire.

It should be noted that the results of the above tests are dependent on the specific sensors used. Since IR sensors are different from each other in terms of their responsivity, the ratios that were measured in Table 1 would be different for different sets of sensors. The different responses can be calibrated, as known in the art, by comparing the responsivity of each sensor with the responsivity of the sensor that was tested, and by adjusting the thresholds accordingly. Generally this is a recommended practice, when producing and calibrating flame detectors according to embodiment of the current invention.

Detection of $SO_2$ Emitting Fires

To detect fires that produce hot $SO_2$ in their combustion process, a sensor which is responsive to the wavelength band in the $SO_2$ spectral peak around 3.96 μm is used. In one embodiment of the present invention, the sensor is sensitive to the wavelength band of 3.95 μm to 4.05 μm Options of this embodiment are described below.

One possible option is where this sensor is used as the $IR_2$ sensor (i.e. for detection of $CO_2$ and $SO_2$ emitting flames). In this case sensor $IR_3$ can be used as in the example described hereinabove (waveband 2.0-2.6 μm). Alternatively or optionally, a sensor having a waveband 3.2-3.5 μm may be used.

Another option is to use the "$SO_2$ sensor" instead of $IR_1$, thereby having a detector that is sensitive to $SO_2$ emitting fires, and $H_2O$ emitting fires.

Another, significantly different option is to have a detector with 5 sensors, where the "$SO_2$ sensor" (for example 3.95-4.05 μm waveband) is added to the other 4 sensors. A third branch in the fire detection algorithm/heuristic (refer to FIG. 2) would be added. In this branch the intensity of the $SO_2$ sensor is compared to a threshold, along with the ratios between it and the two reference sensors (those with wavebands of 2.0-2.6 μm and 4.5-5.0 μm or similar ranges).

Detection of $NO_2$ Emitting Fires

A fire that emits $NO_2$ is yet another example of combustion products that can be similarly detected along with other types of fires, in an embodiment of the present invention described below.

A $NO_2$ fire is detected by measuring its 6.2 μm peak, i.e. using a sensor that has an exemplary sensitivity to the 6.1-6.3 μm wavelength band. In this case, the longer wavelength reference sensor (4.5-5.0 μm) is changed, so that it covers wavelengths longer than the 6.1-6.3 μm waveband. For example, a 7.0-8.0 μm waveband sensor is used.

UV Detection

Detection wavelengths of fires are not limited to the IR part of the spectrum. Detection using UV may also be used. For example, the $SO_2$ peak in the waveband 260-310 nm can be used.

Another example is the detection of H2O emitting flames using the 300-310 nm waveband, exhibited by the emission from hot OH. Since during the combustion process most $H_2O$ emitting fires include hot OH molecules, the flame's spectrum would include a peak around this waveband. Appropriate sensors in embodiments of the present invention may be chosen to yield similar fire determination characteristics, mutatis mutandis.

It will be appreciated that the above descriptions are intended only to serve as examples, and that many other embodiments are possible within the scope of the present invention as defined in the appended claims.

What is claimed is:

1. A method of detecting a fire condition in a monitored region including the operations of:
   (a) concurrently monitoring the region using:
      (i) a single detector having a plurality of fire combustion product emission band sensors, each band sensor sensitive to radiation within a respective waveband which includes at least part of a respective fire combustion product emission band of a plurality of non-identical fire combustion products, the plurality of non-identical fire combustion products equal to n;
      (ii) a first reference band sensor sensitive to radiation within a first reference waveband which includes at least some wavelengths shorter than the n fire combustion product emission bands; and
      (iii) a second reference band sensor sensitive to radiation within a second reference waveband which includes at least some wavelengths longer than the n fire combustion product emission bands; and
   (b) using the band sensors to obtain n+2 measurement values of radiation intensity emitted from the monitored region in determining the presence or absence of the fire condition wherein the n+2 measurement values include: n measurement values obtained from the emission band sensors; one measurement value obtained from the first reference band sensor; and one measurement value obtained from the second reference band sensor and from which detection parameters are calculated, which are evaluated against at least one threshold in determining the presence or absence of the fire condition wherein the detection parameters include two respective reference ratios calculated for each of the n measurement values: a first reference ratio between respective n measurement values and the measurement value from the first reference band sensor; and a second reference ratio between respective n measurement values and the measurement value from the second reference band sensor.

2. The method according to claim 1, wherein the detection parameters further include ratios calculated for each of the n measurement values, between a respective measurement value and other measurement values.

3. The method according to claim 2, wherein the detection parameters further include a first-to-second reference ratio calculated between respective measurement values from the first and second reference band sensors.

4. The method according to claim 1, wherein the detection parameters include two respective correlation values calculated for each of the n measurement values, a first reference correlation between respective n measurement values and the measurement value from the first reference band sensor, and a second reference correlation between respective n measurement values and the measurement value from the second reference band sensor.

5. The method according to claim 1, wherein individual fire combustion products are identified.

6. The method according to claim 1, wherein the at least one threshold includes a threshold value associated with respective measurement values and with respective correlation values.

7. The method according to claim 6, wherein the at least one threshold value is determined by at least one chosen from a list including: empirical means and non-empirical means.

8. The method according to claim 7, wherein n=2 and the plurality of fire combustion products is chosen from a list including: $CO_2$ and $H_2O$, and $CO_2$ and OH, and $SO_2$ and $H_2O$, and $SO_2$, and OH, and $NO_2$ and $H_2O$, and $NO_2$ and OH.

9. The method according to claim 7, wherein n=3 and the plurality of fire combustion products is: $CO_2$ and $H_2O$ and $SO_2$, or $NO_2$ and $H_2O$ and $SO_2$.

10. The method according to claim 1, wherein respective band sensors are sensitive to infrared radiation.

11. The method according to claim 1, wherein respective band sensors are sensitive to ultraviolet radiation.

12. The method according to claim 1, where n=2 and:
   (i) the plurality of fire combustion product emission band sensors includes a first band sensor [$IR_1$], having a sensitivity to a waveband which includes part of the 4.2 to 4.7 μm $CO_2$ emission band, and a second band sensor

[IR₂], having a sensitivity to a waveband which includes at least part of the 2.4 to 3.1 μm H₂O emission band;

(ii) the first reference sensor [IR₃], having a sensitivity to waveband, which includes at least some wavelengths shorter than the wavebands of sensors [IR₁] and [IR₂]; and (iii) the second reference sensor [IR₄], having a sensitivity to waveband, which includes at least some wavelengths longer than the wavebands of sensors [IR1] and [IR2].

13. The method according to claim 12, wherein individual fire combustion products are identified.

14. A method of detecting a fire condition in a monitored region including the operations of:

(a) concurrently monitoring the region using:
(i) a plurality of fire combustion product emission band sensors, each band sensor sensitive to radiation within a respective waveband which includes at least part of a respective fire combustion product emission band of a plurality of non-identical fire combustion products, the plurality of non-identical fire combustion products equal to n;
(ii) a single detector having a first reference band sensor sensitive to radiation within a first reference waveband which includes only wavelengths shorter than the n fire combustion product emission bands; and
(iii) a second reference band sensor sensitive to radiation within a second reference waveband which includes only wavelengths longer than the n fire combustion product emission bands; and (b) using the band sensors to obtain n+2 measurement values of radiation intensity emitted from the monitored region in determining the presence or absence of the fire condition wherein the n+2 measurement values include: n measurement values obtained from the emission band sensors; one measurement value obtained from the first reference band sensor; and one measurement value obtained from the second reference band sensor and from which detection parameters are calculated, which are evaluated against at least one threshold in determining the presence or absence of the fire condition wherein the detection parameters include two respective reference ratios calculated for each of the n measurement values; a first reference ratio between respective n measurement values and the measurement value from the first reference band sensor; and a second reference ratio between respective n measurement values and the measurement value from the second reference band sensor.

* * * * *